United States Patent [19]

Carrier

[11] Patent Number: Plant 5,410

[45] Date of Patent: Mar. 5, 1985

[54] CARNATION PLANT

[76] Inventor: Leonard E. Carrier, 1911 Sheridan Rd., Encinitas, Calif. 92024

[21] Appl. No.: 525,601

[22] Filed: Jun. 22, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—James R. Cypher

[57] ABSTRACT

The present invention relates to a new and distinct cultivar of carnation plant, named Carrier's Fiesta, originated by me by crossing unnamed and unpatented seedlings; distinguished from its parents as well as any other variety known to me by its pink-orange color, its superior resistance to soil borne diseases, and its flowers that open fully without bursting the calyx and causing splits.

1 Drawing Figure

BACKGROUND OF THE INVENTION

The present invention relates to a new and distinct cultivar of carnation plant, named Carrier's Fiesta, which was originated by me by crossing numbered but unnamed and unpatented seedlings.

The new cultivar was the result of a breeding program undertaken by me in my commercial nursery at Encinitas, Calif. by cross-breeding numbered but unnamed and unpatented seedlings; nursery numbers 1981 and 1743.

Typically, carnation plants, botanically known as the species *Dianthus caryophyllus,* are very prone to fungi and root rots, and have a tendency to burst their calyx causing "splits" as the flowers open fully. The primary objectives of this breeding program were to produce a cultivar of "new" color combined with greatly improved resistance to soil-borne diseases and "splitting". These objectives were fully achieved, along with other desirable improvements, as evidenced by the following unique combination of principal characteristics which are outstanding in my new cultivar, Carrier's Fiesta, and which distinguish it from its parents, as well as from all other carnations of which I am aware:

1. Superior resistance to soil-borne diseases such as *Fusarium oxysporium,* and *F. roseum* and root-rots such as damping off, water molds, and the like;
2. Large serrated flowers which open fully without bursting the calyx and causing "splits";
3. A distinctive and attractive pink-orange flower color which fades slightly to peach, or strawberry pink.

The closest commercial variety to which it compares is Tangerine.

Asexual reproduction of my new carnation variety by side shoot cuttings rooted in peat and "Perlite" under mist, as performed under my direction and control at Encinitas, Calif., shows that the foregoing characteristics and distinctions come true and are established and transmitted through succeeding propagations.

BRIEF DESCRIPTION OF THE DRAWING

The accompanying color photograph shows typical specimens of the new cultivar in different stages of development (tight buds, partially opened bud and full bloom) and illustrates the vigorous, free-breaking growth habit and strong, straight stems.

The color photo submitted is the one that applicant feels most nearly shows the true color of his new cultivar, and close inspection of the two larger blooms shows the dark pink stripe in the petals of the flowers.

DETAILED DESCRIPTION OF THE DRAWING

The following is a detailed description of my new carnation cultivar, Carrier's Fiesta, with color terminology in accordance with Robert Ridgway's Color Standards and Nomenclature (1912 edition).

The following detailed botanical description is based on observations of plants grown inside my commercial grenhouses at Encinitas, Calif.: the height of plant and flower and foliage size established as an average using standard commercial cultural practices.

The data provided accurately characterizes the cultivar in question. Color designation and other values stated may deviate slightly from the stated values from flowering to flowering, but the deviations will be within the range expected from varying environmental, seasonal, and cultural conditions. Applicant has noted that the cooler temperatures of winter causes the flower color to be slightly more orange and less strawbery pink, and the warmer days of summer cause the flower color to be slightly more strawberry pink and less orange. Just the opposite from what one in the floral industry would expect.

PLANT

Botanical classification: *Dianthus caryophyllus.*

Breeding:

*Female parent.*—Nursery Number 1743.

*Male parent.*—Nursery Number 1981.

Form: Erect but free-branching.

Growth: Vigorous and very free-branching.

Height: Medium tall, approximtely 80 to 100 cm.

Classification: Greenhouse type, suitable for cut flower production as a standard (one bloom per stem).

Propagation: Holds its distinguishing characteristics through succeeding propagations by rooted cuttings.

Locality where grown and observed: Encinitas, Calif.

Disease resistance: The new cultivar has shown no evidence of fusariums or other root rots, as determined by extensive tests in high infested soils inoculated with as many strains of fungi as are locally available in the area of Encinitas, Calif.; tested conducted without chemical or steam sterilization of the soil (soils in which the carnation plant "Sim" and others soon die).

Blooming period: The new cultivar will bloom at any time of the year in California.

Temperature tolerance: Not hardy to cold and will freeze at −10° C. Grows best at 10° C. but has good resistance to hot weather in summer months without hardening of growth and with only little reduction in flower size and fading. Cooler temperatures of winter causes the flower color to be slightly more orange and less strawberry pink, and the warmer days of summer cause the flower color to be slightly more strawberry pink and less orange.

BUD

Lobes of calyx overlap in tight bud and seldom split.

Length: 2.5 cm.

Diameter: 2.5 cm.

BLOOM

Size: 8 cm. diameter, depth 2.5 cm.

Stem: Consists of 9 nodes. Length is about 60 cm. Diameter is about 0.8 cm. at base and about 0.4 cm. at base of calyx. Color is Yew green Plate XXXI 27″ G-Y m. Yew green.

Form: Generally round with high, well developed crown when fully opened, calyx is completely hidden.

Petalage: From 80–90 petals. Outer petals are approximately 4.0 cm. wide and about 5.0 cm. long. Center petals are about 2.0 cm. wide and about 4.0 cm. long.

Color: The center of flower, outer petals, base of petals, Plate I 5 00-R Strawberry Pink. Back of petal Plate II 7. R-O d Grenadine Pink. Petals have a dark pink streak Plate I 3 O-R Nepal Red.

General tonality: Pinkish orange with a dark pink streak.

Petals: Texture is soft but firm.

*Form.*—Outer petals nearly semi-circular with roughly uniform serrations of 0.4 cm. to 0.1 cm. deep 6 to 8 per cm.

*Opening.*—Outer petals expand before the center petals. The calyx is very strong and there is a minimum of split calyx.

Fragrance: No distinctive fragrance.

FOLIAGE

Form: Concave to flat.

Size: 1 cm. wide and 19 cm. long.

Quantity: Two leaves per node, with nodes spaced about 5 cm. apart.

Color: The upper and under sides of mature leaves are Yew green Plate XXXI 27″. G-Y M. Yew Green. New Growth Rainette Green 27″ G-Y i, Rainette Green.

Texture: Smooth.

I claim:

1. A new and distinct cultivar of carnation plant named, Carrier's Fiesta, substantially as herein shown and described, characterized particularly as to novelty by the unique combination of superior resistance to soil-borne diseases; large, slightly serrated flowers which open fully without bursting the calyx and causing "splits"; a distinctive and attractive pink-orange flower color which fades evenly and beautifully; a very vigorous and free-breaking plant habit; strong and straight stems; and good heat tolerance which is superior to that of the parent lines and the commercial standard, the so-called "Sim".

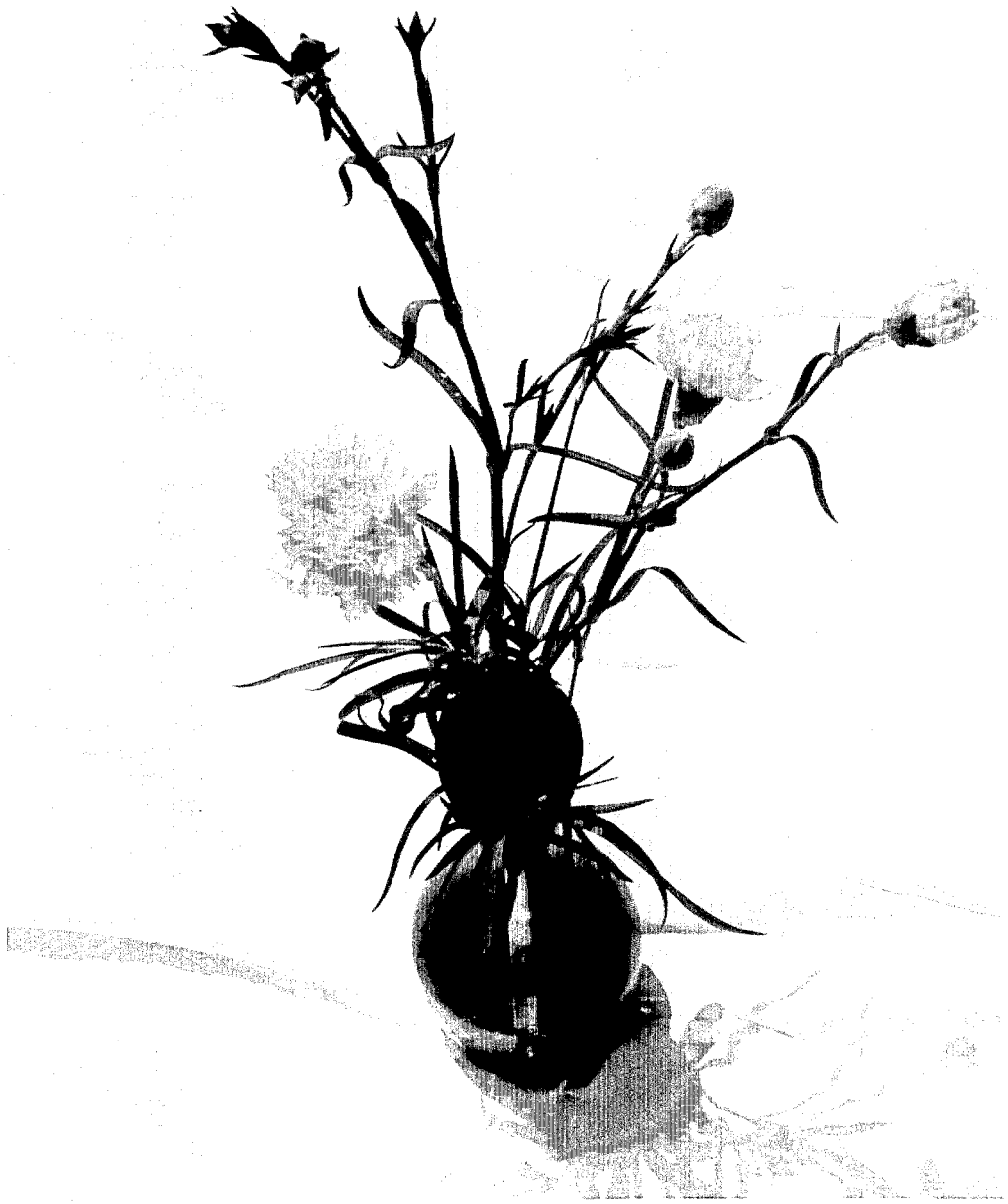

* * * * *